United States Patent [19]

Kamiyama et al.

[11] Patent Number: 4,712,895
[45] Date of Patent: Dec. 15, 1987

[54] OCULAR POSITION MEASURING APPARATUS

[75] Inventors: Kiichi Kamiyama; Yasuo Kato, both of Tokyo, Japan

[73] Assignee: Tokyo Kogaku Kikai Kabushiki Kaisha, Tokyo, Japan

[21] Appl. No.: 664,507

[22] Filed: Oct. 25, 1984

[30] Foreign Application Priority Data

Oct. 26, 1983 [JP] Japan ................. 58-200519

[51] Int. Cl.⁴ .................. A61B 3/02; A61B 3/10
[52] U.S. Cl. ..................... 351/243; 351/204; 351/211
[58] Field of Search ............ 351/205, 201, 202, 204, 351/209, 210, 211, 243

[56] References Cited

U.S. PATENT DOCUMENTS

| | | | |
|---|---|---|---|
| 1,327,163 | 1/1920 | Mathewson et al. | 351/204 |
| 3,454,331 | 7/1969 | Maitenaz | 351/204 |
| 4,179,195 | 12/1979 | Krumeich | 351/202 |
| 4,372,655 | 2/1983 | Matsumura | 351/211 |
| 4,465,348 | 8/1984 | Lang et al. | 351/211 |

Primary Examiner—Rodney B. Bovernick
Attorney, Agent, or Firm—Brumbaugh, Graves, Donohue & Raymond

[57] ABSTRACT

An ocular position measuring apparatus comprising a pair of fixation marks capable of emitting visible flickering beams for being watched by patient, a first pair of half mirrors positioned between the patient's eyes and the marks and an observing system for observing images of the patient's eyes on produced by light beams reflected by the half mirrors.

2 Claims, 6 Drawing Figures

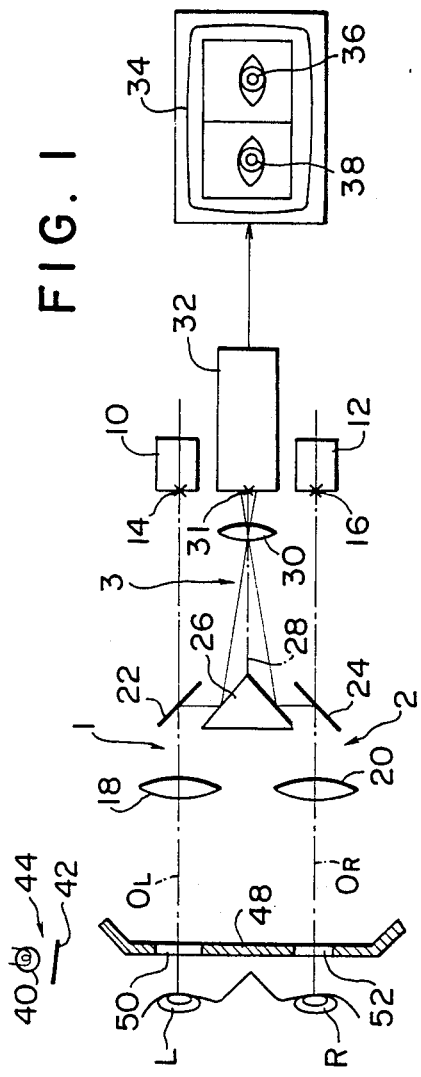
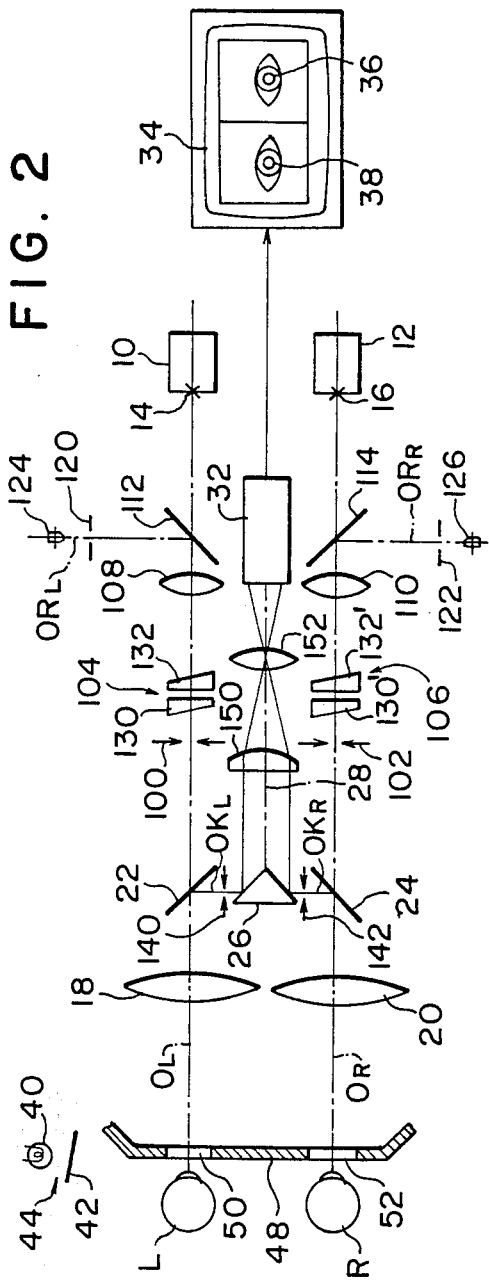

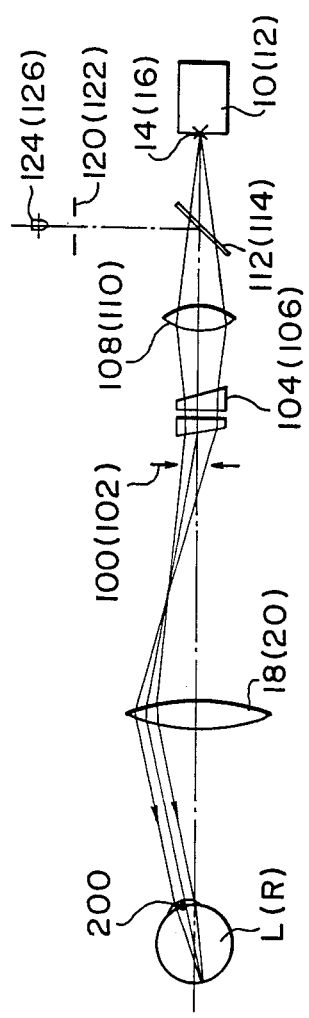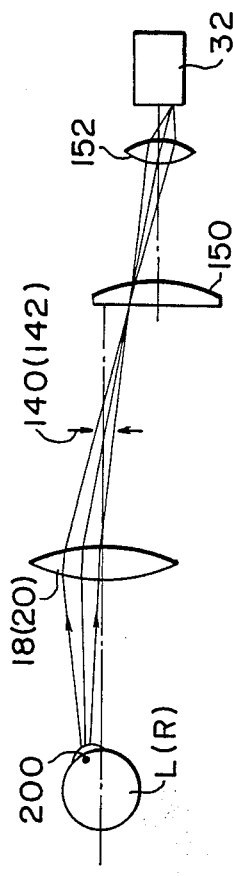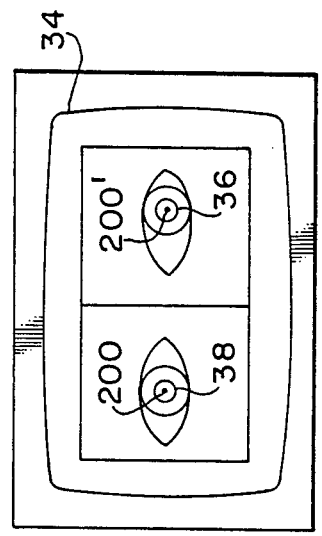
FIG. 3
FIG. 4
FIG. 5

OCULAR POSITION MEASURING APPARATUS

BACKGROUND OF THE INVENTION

1. Field of the Invention

The present invention relates to a ocular position measuring apparatus and more particularly to instruments for examining patient's eyes for heterophoria and strabismus for example, phorometers or phoro-optimeters. More specifically, the present invention pertains to instruments having a pair of flickering marks emitting visible beams which are to be fixed upon by a patient.

2. Description of Prior Art

Abnormality of ocular position is generally classified into two categories, one being the heterophoria in which an eye deviates from the normal position with respect to the line of vision when the eyes are located in rest position and which can be eliminated through a binocular fusion, and the other being strabismus in which one of the eyes is unable to obtain binocular vision with the other because of an imbalance of the extraocular muscles.

In a conventional method for examining abnormality of the ocular position, a cross mark in located at a distance of for example 5 meters or more for examining a farsighted heterophoria and a small lamp or a toy is located at a distance of for example 33 centimeters for examining a near-sighted heterophoria. In both cases, a rectangular cardboard sheet of 15 centimeters by 25 centimeters is used as a blocking member which is to be inserted in front of a patient's eye while letting the patient watch the aforementioned marks. The movement of the pupil of the eye blocked by the blocking member is then inspected to determined whether there is a heterophoria.

In performing this inspection, it is desirable that the inspector sits in front of the patient in order to precisely inspect the movement of the pupil. It should however be noted that, since the inspector sitting in front of the patient may possibly block the patient's sight, the inspector is obliged to observe the patient's eyes from a front lower position. It should further be noted that in performing this type of inspection it is desirable that the eyes be at a complete rest, without any binocular fusion or accommodation when the blocking member is in front of an eye. Therefore, it is important to carry out the inspection in a completely dark room so that the patient cannot watch anything except the fixation mark. It should however be noted that the inspection must be actually made in a half dark room since the inspector must visually observe the movement of the patient's eye. Thus, there have been problems of inaccuracy of examination owing to binocular fusion and accommodation of the patient's eyes, and the difficulty of the observation of the patient's pupils in the half dark room.

As an alternative procedure for inspecting an abnormality of ocular position, there has been known an amblyoscope which is designed to make it possible for the inspector visually inspect movements of the patient's eyes. However, the amblyoscope has an eyepiece which has to be placed so that in front of the patient's eye, it is difficult to inspect the movement of the patient's eye.

It has also been known to use a phase difference haploscope for inspecting the abnormality of ocular position. The haploscope comprises a pair of rotating sectors which are adapted to be positioned in front of the patient's eyes and rotated at a high speed with 90° phase difference with each other. A screen is provided for projecting visible images for both eyes through a pair of projecting sectors which are synchronized with the rotating sectors, so that the patient's eyes can catch only the images corresponding to the eyes, respectively. This type of inspecting instrument is however disadvantageous because the rotating sectors located in front of the patient's eyes make it difficult to inspect the patient's eyes.

DESCRIPTION OF THE INVENTION

1. Object of the Invention

It is an object of the present invention to provide a measuring apparatus for inspecting a heterophoria and-/or a strabismus, which is free from the problems inherent to the conventional instruments.

Another object of the present invention is to provide an ocular position measuring apparatus which makes it possible to observe movements of the patient's eyes from the front without any binocular fusion and accommodation.

Still another object of the present invention is to provide an ocular position measuring apparatus which can provide an accurate measurement.

A further object of the present invention is to provide an ocular position measuring apparatus which is designed to produce bright marks at the centers of images of the pupil of the patient's eyes so that a reading of movements of the pupils can be made.

Still further object of the present invention is to provide an ocular position measuring apparatus which can perform inspections without any binocular fusion and accommodation even in a light room.

2. Summary of the Invention

According to the present invention, the above and other objects can be accomplished by an ocular position measuring apparatus comprising a pair of fixation mark means capable of emitting visible flickering beams for being watched by patient's eyes, a first pair of half mirrors positioned between respective ones of the patient's eyes and the mark means, observing means for observing images of the patient's eyes reflected by the half mirrors.

In a preferable aspect of the present invention, the ocular position measuring apparatus may further include an infrared light source for illuminating the eyes, the half mirrors being of a type that reflect infrared rays and transmit visible rays. The observing means may then have image pick-up means, an optical member for guiding the beams reflected by the half mirrors to the image pick-up means, and display means for displaying images of the patient's eyes in accordance with the output of the image pick-up means. The ocular position measuring apparatus may include a pair of variable deflection prisms between the half mirrors and the fixation mark means. The phorometer may further include a pair of second half mirrors reflecting infrared rays and transmitting visible rays between the variable deflection prisms and the gazing mark means, and a pair of mark members located along the paths of the beams reflected by the second half mirrors.

According to another aspect of the present invention, the above and other objects can also be accomplished by an ocular position measuring apparatus having a pair of flickering and fixation mark means for projecting fixation marks of visible rays onto patient's eyes, a pair of first half mirrors located between respective ones of the eyes and respective ones of the fixation mark means along right and left fixation axes, a pair of variable deflection prisms located between respective ones of the first half mirrors and the fixation mark means along the right and left fixation axes, a pair of second half mirrors located between the variable deflection prisms and the fixation mark means along the right and left fixation axes and capable of reflecting infrared rays and transmitting visible rays, a pair of infrared mark members located along reflecting axes of the second half mirrors to project images of the infrared marks on the eyes, position detecting means for detecting position of the image of the infrared marks produced by light beams reflected by the eyes, a control circuit for controlling rotation of the variable deflection prisms when the image of the infrared mark moves in response to flicking of one of the fixation marks, whereby quantity and direction of heterophoria and strabismus are detected from the position of the infrared mark and direction and quantity of deflection of the variable deflection prisms when the image of the infrared mark does not move in response to flickering of the fixation mark.

The above and other objects and features of the present invention will become apparent from the following descriptions of preferred embodiments with reference to the accompanying drawings.

BRIEF DESCRIPTION OF THE DRAWINGS

FIG. 1 is a diagrammatic illustration of an optical system of a first ocular position measuring apparatus in which the present invention is embodied;

FIG. 2 is a diagrammatic illustration of an optical system of a second ocular position measuring apparatus in which the present invention is embodied;

FIG. 3 is a diagrammatic illustration of a mark projecting system in the second ocular position measuring apparatus;

FIG. 4 is a diagrammatic illustration of an observing system in the second ocular position measuring apparatus;

FIG. 5 shows a CRT display for displaying images of the right and left eyes;

DESCRIPTION OF THE PREFERRED EMBODIMENTS

Figure 6:
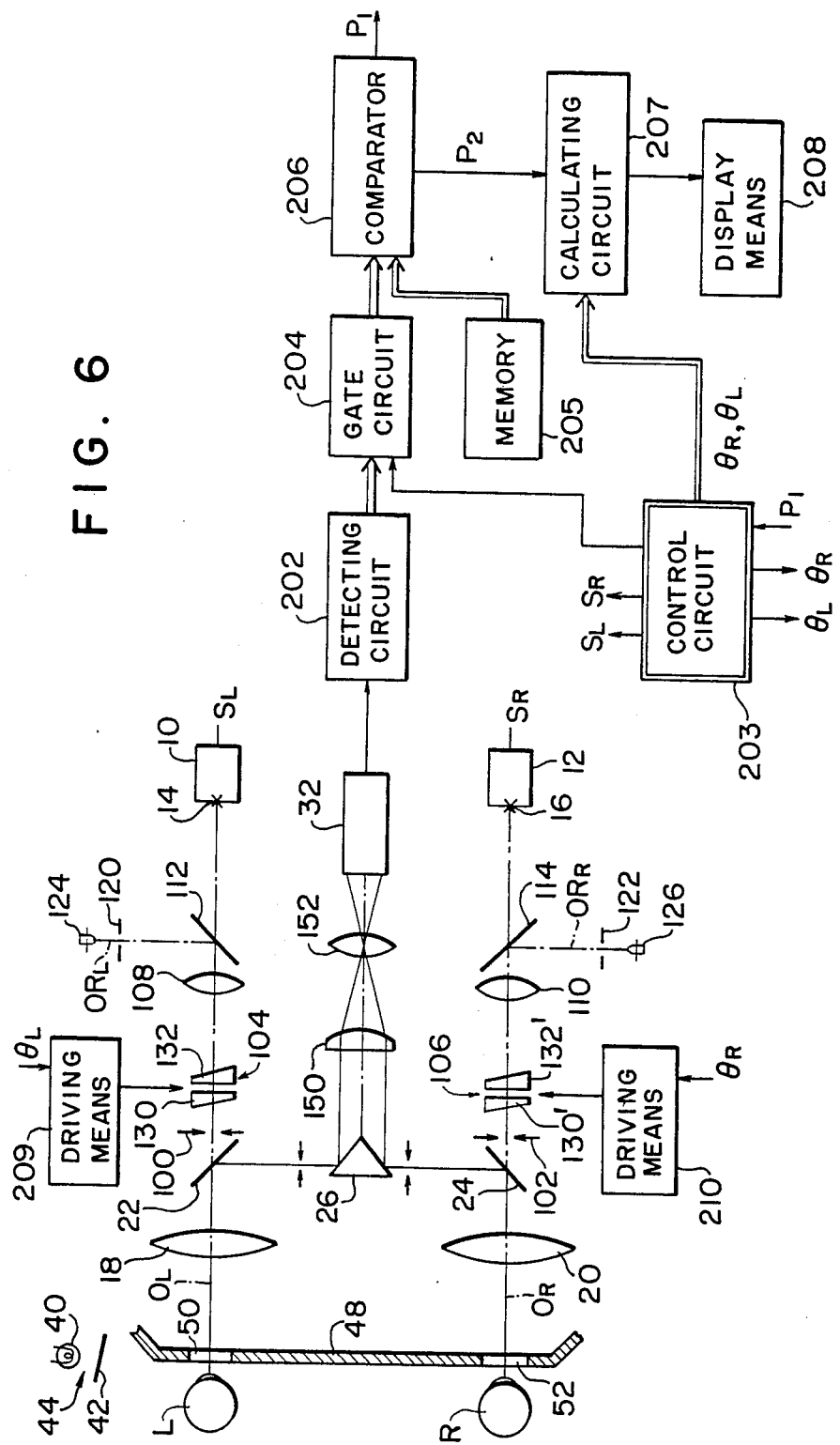
FIG. 6 is a diagrammatic illustration of an optical system of a third ocular position measuring apparatus in which the present invention is embodied.

Referring now to the drawings, there are shown three different embodiments of ocular position measuring apparatus.

The first apparatus, as shown in FIG. 1, includes a left fixation mark system 1, a right fixation mark system 2, and an imaging system 3. The left fixation mark system 1 and the right fixation mark system 2 have flickering mark units 10, 12 on mark projecting optical axes $O_L$, $O_R$. The patient's left and right eyes L, R are respectively aligned with the optical axes $O_L$ and $O_R$. The fixation axes $O_L$, $O_R$ are made parallel in order to examine far-focusing eyes. Between the eyes L, R and the units 10, 12, there are located objective lenses 18, 20 respectively. The units 10, 12 are movable along the axes $O_L$, $O_R$ and adjusted so that the fixation marks 14, 16 are located conjugate with the retinas of the eyes L, R with respect to the objective lenses 18, 20, respectively.

The imaging system 3 has half mirrors 22, 24 which are obliquely located between the objective lenses 18, 20 and the units 10, 12. The half mirrors 22, 24 reflect infrared rays and pass visible rays. The imaging system 3 further has a right angle prism 26 located along the paths of the beams reflected by the half mirrors 22, 24, a condenser lens 30, and an infrared camera tube 32, both of which are located along the imaging axis 28 of the beam reflected by the prism 26. The tube 32 is located conjugate with the front portions of the eyes L, R with respect to the lenses 18, 20. The tube 32 has an output connected with a cathode ray tube 34 which shows a right image 36 and a left image 38 of the pupils of the eyes L, R.

The aforementioned systems 1, 2, 3 are mounted in a dark housing 48 which has openings 50, 52, as shown in FIG. 1. Obliquely to the front of the eyes L, R, there is provided an infrared illuminating means 44 which includes a tungsten lamp 40 and an infrared filter 42 located in front of the lamp 40, so that the eyes L, R are obliquely illuminated by an infrared ray.

In the aforementioned first apparatus, the eyes L, R are fixed at the fixation marks 14, 16 through the openings 50, 52. When the fixation marks 14, 16 turn off, the eyes L, R can have nothing upon which to become affixed so that they assume a nonfusion and unfixation state. However, as the images 36, 38 always appears on the tube 34, the movement of the images 36, 38 corresponding to the flickering of the marks 14, 16 can be examined. For example, when the mark 14 is lit continuously and the mark 16 flickers, heterophoria appears as the distance and the direction of any movement of the image 38 of the right eye's pupil.

The second embodiment of the ocular position measuring apparatus is shown in FIG. 2. In this embodiment, elements corresponding to those described above are given with the same reference numerals and explanations thereof are omitted. Between the half mirrors 22, 24 and the units 10, 12, there are provided circular aperture members 100, 102, rotary prisms 104, 106, relay lenses 108, 110, and half mirrors 112, 114 which reflect infrared rays and pass visible rays, in this order from the half mirrors 22, 24 to the units 10, 12. The aperture members 100, 102 are located conjugate with the pupils of the eyes L, R with respect to the lenses 18, 20, and the prisms 104, 106 are located conjugate with the positions that would be assumed by any glasses worn by the patient with respect to the lenses 18, 20 respectively.

On axes $OR_L$, $OR_R$ of the beams reflected by the half mirrors 112, 114, there are provided pinhole members 120, 122 which are located conjugate with the lenses 18, 20, 108, 110 with respect to the pupils of the eyes L, R, and which are illuminated by infrared LEDs 124, 126, respectively. The pinhole members 120, 122 produce bright points on the corneas of the eyes L, R. The rotary prisms 104, 106 comprise identical deflection prisms 130, 132, 130', 132' which are adapted to be rotated in directions opposite to each other, so that the rotary prisms 104, 106 provide deflection angles between zero and twice as large as the deflection angle of one of the prisms 130, 132, 130', 132'.

On axes $OK_L$, $OK_R$ reflected by the half mirrors 22, 24, there are provided circular aperture members 140, 142 located at focusing positions of the lenses 18, 20. The beams having axes $OK_L$, $OK_R$ are reflected by the prisms 26 and become a beam having an axis 28. On the axis 28, there are provided a field lens 150 the front focusing point of which is located at the positions of the aperture members 140, 142, and an objective lens 152 the rear focusing point of which is positioned at the tube 32. A telecentric optical system is constituted by the lenses 18, 20, the aperture members 140, 142, and the lenses 150, 152, so that the front portions of the eyes L, R can be precisely examined even if the eyes L, R should be incorrectly positioned with respect to the axes $O_L$, $O_R$.

In the aforementioned second apparatus, the rotary prisms 104, 106 are adjusted so that deflection angle thereof becomes zero, the eyes L, R are fixed at the flickering mark 14 and the lighting mark 16 through the openings 50, 52, respectively. If the eyes L, R do not have heterophoria, the images 36, 38 are directed right forward and the bright points at the centers of the pupils of the eyes appear on the tube 34.

Referring also to FIG. 5, if the eyes L, R have heterophoria, the image 38 on the tube 34 moves in response to flickering of the mark 14. In this case, the rotary prism 104 is adjusted so that the image 38 on the tube 34 does not move with regard to the stationary pinhole image 200 even though the fixation mark 14 flickers. in Describing more specifically, as shown in FIG. 3, the beams from the fixation mark 14 and the pinhole member 120 abut to the obliquely resting eye L through the rotary prism 104 adjusted as mentioned above, and the image of the eye L, as shown in FIG. 4, is produced on the tube 32 through the telecentric optical system. On the other hand, the beams from the fixation mark 16 and the pinhole member 122 abut to the eye R along axis $O_R$ through the zero deflection rotary prisms 106, and the image of the eye R is produced on the tube 32 through the telecentric optical system.

On the tube 34, as shown in FIG. 5, there are produced the stationary image 38 of the pupils directed to the front, and the stationary image 36 of the eye L directed one side. These images 36, 38 include the pinhole images at their center. In this condition, heterophoria is quantitatively shown by the deflection angle and the deflection direction of the prism 104.

In the aforementioned first and second apparatus, the inspector measures the heterophoria in accordance with the movement of the pupil images on the tube 34. The third embodiment of the ocular position measuring apparatus, however, is constituted so that movement of the pupil images is photo-electrically detected to automatically calculate the quantity and angle of heterophoria.

The third embodiment of the phorometer, as shown in FIG. 6, has the same optical system as the second apparatus does, and therefore, optical elements corresponding to those in the second apparatus are designated by the same reference numerals and explanations thereof are omitted.

A control circuit 203 has outputs connected with the units 10, 12 and applies a first flickering signal SL for slowly flickering the mark 14 to the unit 10, and a lighting signal $S_R$ for continuously lighting the mark 16 to the unit 12, respectively. The control circuit 203 also has outputs connected with prism driving means 209, 210 for rotating the prisms 104, 106, respectively. At this time, the prism 104, 106 are adjusted to a deflection angle of zero degree. A position detecting circuit 202 takes a scan output signal from the tube 32 and functions to detect positions of the pinhole images, the beams of which are reflected at the cornea of the eye L and in synchronized with a lit or unlit state of the mark 14. A gate circuit 204 has an output connected with the circuits 202, 203 to receive pupil image position signals and the gate control signal, respectively, and functions to transfer the position signal for the lit state of the mark 14 to a memory 205 and the position signal for the unlit state of the mark 14 to a comparator 206 in accordance with a control signal produced by the control circuit 203.

The comparator 206 has inputs connected with the gate circuit 204 and the memory 205 to receive the position signals, and functions to compare the position signals. When the position signals are not the same, the comparator 206 produces a signal $P_1$, which is supplied to the control circuit 203 so that the driving means 209 is applied with the signal $\theta L$, from the control circuit 203, which increases the deflection angle of the prism 104 by a predetermined degree in the direction from the pinhole image position at the time the mark 14 is lit to the pinhole image position at the time the mark is unlit.

The aforementioned operation is repeated till the position signals from the gate circuit 204 and the memory 205 become the same, or the pupil images on tube 32 are produced at the same position regardless of whether the mark 14 is lit or unlit. When the position signals are the same, the comparator 206 produces a signal $P_2$ which is supplied to the a calculating circuit 207. The calculating circuit 207 has an input connected with the control circuit 203 to receive the signal $\theta L$ and functions to calculate the quantity and the angle of the heterophoria from the signal L. Display means 208 take an output from the circuit 207 and functions to display the quantity and the angle of the heterophoria.

In the aforementioned first, second and third embodiments, the quantity and the angle of the strabismus are also measured in the same manner as mentioned above, and the heterophoria and the strabismus are experimentally distinguished by the movements of the images 36, 38 in response to the fixation mark.

The invention has thus been shown and described with reference to specific embodiments. However, it should be noted that the invention is in no way limited to the details of the illustrated arrangements but changes and modifications may be made without departing from the scope of the appended claims.

We claim:

1. An ocular position measuring apparatus for determining the heterophoria or strabismus of a patient's eyes, having a pair of fixation mark means for projecting fixation marks of visible rays into patient's eyes, a pair of first half mirrors located between respective ones of the eyes and respective ones of the fixation mark means along right and left fixation axes, a pair of rotatable variable deflection prisms located between respective ones of the first half mirrors and the fixation mark means along the right and left fixation axes, a second pair of half mirrors located between the variable deflection prisms and the fixation mark means along the right and left fixation axes and capable of reflecting infrared rays and transmitting visible rays, a pair of infrared mark members located along reflecting axes of the second pair of half mirrors to project images of the infrared marks on the eyes, position detecting means for detecting position of the image of the infrared marks produced by light beams reflected by the eyes, a control circuit for controlling rotation of the variable deflection prisms when the image of the infrared mark moves in response to the flickering of one of the fixation marks, whereby quantity and direction or angle of heterophoria and strabismus are detected from the position of the infrared mark and direction or angle and quantity of deflection of the variable deflection prisms when the image of the infrared mark does not move in response to flickering of the fixation mark.

2. An ocular position measuring apparatus for determining the heterophoria or strabismus of a patient's eyes, having a pair of fixation mark means for projecting fixation marks of visible rays into patient's eyes, a pair of first half mirrors located between respective ones of the eyes and respective ones of the fixation mark means along right and left fixation axes, a pair of rotatable variable deflection prisms located between respective ones of the first half mirrors and the fixation mark means along the right and left fixation axes, driving means for automatically rotating said deflection prisms, a second pair of half mirrors located between the variable deflection prisms and the fixation mark means along the right and left fixation axes and capable of reflecting infrared rays and transmitting visible rays, a pair of infrared mark members located along reflecting axes of the second pair of half mirrors to project images of the infrared marks on the eyes, position detecting means for detecting position of the image of the infrared marks produced by light beams reflected by the eyes, a control circuit responsive to a movement of the image of the infrared mark when one of the fixation marks is flickering for controlling said driving means, circuit means for alternately receiving image position signals from said position detecting means when said mark means are in a lit or unlit state and, comparator circuit means for comparing said position signal received when the mark is in a lit state with said position signal received when the mark is in an unlit state, and applying a signal to said control circuit for rotating said variable deflection prisms when said lit and unlit position signals are not the same, , whereby quantity and direction or angle of heterophoria and strabismus are detected from the position of the infrared mark and direction or angle and quantity of deflection of the variable deflection prisms when the image of the infrared mark does not move in response to flickering of the fixation mark.

* * * * *